(12) United States Patent
Mamedov et al.

(10) Patent No.: US 11,148,985 B2
(45) Date of Patent: Oct. 19, 2021

(54) PROCESS FOR OXIDATIVE CONVERSION OF METHANE TO ETHYLENE

(71) Applicants: Sabic Global Technologies, B.V., Bergen op Zoom (NL); Aghaddin Mamedov, Sugar Land, TX (US); David West, Sugar Land, TX (US); Vidya Sagar Reddy Sarsani, Sugar Land, TX (US); Wugeng Liang, Sugar Land, TX (US)

(72) Inventors: Aghaddin Mamedov, Sugar Land, TX (US); David West, Sugar Land, TX (US); Vidya Sagar Reddy Sarsani, Sugar Land, TX (US); Wugeng Liang, Sugar Land, TX (US)

(73) Assignee: Sabic Global Technologies, B.V., Bergen op Zoom (NL)

( * ) Notice: Subject to any disclaimer, the term of this patent is extended or adjusted under 35 U.S.C. 154(b) by 2 days.

(21) Appl. No.: 16/481,790

(22) PCT Filed: Jan. 29, 2018

(86) PCT No.: PCT/US2018/015669
§ 371 (c)(1),
(2) Date: Jul. 29, 2019

(87) PCT Pub. No.: WO2018/144370
PCT Pub. Date: Aug. 9, 2018

(65) Prior Publication Data
US 2019/0389788 A1   Dec. 26, 2019

Related U.S. Application Data

(60) Provisional application No. 62/452,732, filed on Jan. 31, 2017.

(51) Int. Cl.
C07C 2/84 (2006.01)
C07C 4/02 (2006.01)
C01B 3/36 (2006.01)

(52) U.S. Cl.
CPC .................. *C07C 2/84* (2013.01); *C01B 3/36* (2013.01); *C01B 2203/0222* (2013.01);
(Continued)

(58) Field of Classification Search
None
See application file for complete search history.

(56) References Cited

U.S. PATENT DOCUMENTS

| 4,128,595 A | 12/1978 | Montgomery |
| 5,025,108 A | 6/1991 | Cameron et al. |

(Continued)

FOREIGN PATENT DOCUMENTS

| RU | 2502717 C1 | 12/2013 |
| WO | 2015057753 A1 | 4/2015 |

(Continued)

OTHER PUBLICATIONS

Galadima, Ahmad, et al., "Revisiting the oxidative coupling of methane to ethylene in the golden period of shale gas: A review", Journal of Industrial and Engineering Chemistry, 2016, pp. 1-13, vol. 37, Elsevier, B.V.

(Continued)

*Primary Examiner* — Philip Y Louie
(74) *Attorney, Agent, or Firm* — Rodney B. Carroll; Conley Rose, P.C.

(57) ABSTRACT

A process for producing ethylene and syngas comprising reacting, via OCM, first reactant mixture ($CH_4$ & $O_2$) in first reaction zone comprising OCM catalyst to produce first product mixture comprising ethylene, ethane, hydrogen, $CO_2$, CO, and unreacted methane; introducing second reac- (Continued)

tant mixture comprising first product mixture to second reaction zone excluding catalyst to produce second product mixture comprising ethylene, ethane, hydrogen, CO, $CO_2$, and unreacted methane, wherein a common reactor comprises both the first and second reaction zones, wherein ethane of second reactant mixture undergoes cracking to ethylene, wherein $CO_2$ of second reactant mixture undergoes hydrogenation to CO, and wherein an amount of ethylene in the second product mixture is greater than in the first product mixture; recovering methane stream, ethane stream, $CO_2$ stream, ethylene stream, and syngas stream ($CO\&H_2$) from the second product mixture; and recycling the ethane stream and the carbon dioxide stream to second reaction zone.

20 Claims, 1 Drawing Sheet

(52) U.S. Cl.
CPC ............. *C01B 2203/0261* (2013.01); *C01B 2203/0283* (2013.01); *C01B 2203/046* (2013.01); *C01B 2203/0415* (2013.01); *C01B 2203/0475* (2013.01); *C01B 2203/061* (2013.01); *C01B 2203/068* (2013.01); *C01B 2203/142* (2013.01); *C01B 2203/148* (2013.01)

(56) References Cited

U.S. PATENT DOCUMENTS

| | | | |
|---|---|---|---|
| 5,430,219 A | 7/1995 | Sanfilippo et al. | |
| 8,080,697 B2 | 12/2011 | Lin et al. | |
| 9,334,204 B1 | 5/2016 | Radaelli et al. | |
| 2004/0013605 A1* | 1/2004 | Ramani | C01B 3/386 423/651 |
| 2010/0016454 A1* | 1/2010 | Gracey | C07C 29/1518 518/703 |
| 2011/0240926 A1 | 10/2011 | Schellen et al. | |
| 2015/0152025 A1* | 6/2015 | Cizeron | C07C 2/78 585/324 |
| 2015/0210610 A1* | 7/2015 | Rafique | B01J 35/0013 585/315 |
| 2016/0272556 A1 | 9/2016 | Rafique et al. | |
| 2016/0376148 A1 | 12/2016 | Mamedov et al. | |
| 2017/0226029 A1* | 8/2017 | Mamedov | B01J 35/0006 |
| 2017/0313584 A1* | 11/2017 | Mamedov | C07C 5/48 |

FOREIGN PATENT DOCUMENTS

| | | |
|---|---|---|
| WO | 2016012371 A1 | 1/2016 |
| WO | 2018144370 A1 | 8/2018 |

OTHER PUBLICATIONS

Krylov, O.V., et al., "Heterogeneous catalytic reactions of carbon dioxide", Russian Chemical Reviews, 1995, pp. 877-900, vol. 64, No. 9, Russian Academy of Sciences and Turpion Ltd.

Krylov, O.V., et al., "The regularities in the interaction of alkanes with CO2 on oxide catalysts", Catalysis Today, 1995, pp. 371-375, vol. 24, Elsevier.

Mamedov, A. Kh., et al., Petrochemistry, Nephtechimiya, 1988, pp. 786-790, vol. 28, No. 6.

Mamedov, A. Kh., et al., "Intermediate Oxygen-Containing Compounds in Oxidative Condensation of Methane Over Sodium-Manganese Catalysts", React. Kinet. Catal. Lett., 1991, pp. 283-289, vol. 45, No. 2, Akadémiai Kiadó.

Mamedov, A. Kh., et al., "Selective Dehydrogenation of Ethane by Carbon Dioxide Over Fe—Mn Oxide Catalyst. An Insitu Study of Catalyst Phase Composition and Structure", New Developments in Selective Oxidation, 1990, pp. 477-482, Elsevier Science Publishers, B.V.

Wolf, E.E., "Overall Performance of the Conceptual OXCO Process", Methane conversion by oxidative processes: fundamental and engineering aspects, Van Nostrand Reinhold Catalysis Series, 1992, pp. 458-459, Springer Science + Business Media LLC.

Filing Receipt and Specification of U.S. Appl. No. 62/452,732, entitled "Process for Oxidative Conversion of Methane to Ethylene", filed Jan. 31, 2017, 44 pages.

Foreign communication from a related application—International Search Report and Written Opinion of International Application No. PCT/US2018/015669, dated Jul. 12, 2018, 14 pages.

Foreign communication from a related application—International Preliminary Report on Patentability of International Application No. PCT/US2018/015669, dated Aug. 15, 2019, 10 pages.

\* cited by examiner

PROCESS FOR OXIDATIVE CONVERSION OF METHANE TO ETHYLENE

CROSS REFERENCE TO RELATED APPLICATIONS

This application is a filing under 35 U.S.C. 371 of International Application No. PCT/US2018/015669 filed Jan. 29, 2018, entitled "A Process for Oxidative Conversion of Methane to Ethylene" which claims priority to U.S. Provisional Application No. 62/452,732 filed Jan. 31, 2017, which applications are incorporated by reference herein in their entirety.

TECHNICAL FIELD

The present disclosure relates to methods of producing hydrocarbons and syngas, more specifically methods of producing olefins, such as ethylene, and syngas by oxidative coupling of methane.

BACKGROUND

Hydrocarbons, and specifically olefins such as ethylene ($C_2H_4$), are typically building blocks used to produce a wide range of products, for example, break-resistant containers and packaging materials. Currently, for industrial scale applications, ethylene is produced by heating natural gas condensates and petroleum distillates, which include ethane and higher hydrocarbons, and the produced ethylene is separated from a product mixture by using gas separation processes.

Oxidative coupling of the methane (OCM) has been the target of intense scientific and commercial interest for more than thirty years due to the tremendous potential of such technology to reduce costs, energy, and environmental emissions in the production of $C_2H_4$. As an overall reaction, in the OCM, $CH_4$ and $O_2$ react exothermically over a catalyst to produce $C_2H_4$, water ($H_2O$) and heat.

Ethylene can be produced by OCM as represented by Equations (I) and (II):

Oxidative conversion of methane to ethylene is exothermic. Excess heat produced from these reactions (Equations (I) and (II)) can push conversion of methane to carbon monoxide and carbon dioxide rather than the desired $C_2$ hydrocarbon product (e.g., ethylene):

The excess heat from the reactions in Equations (III) and (IV) further exasperate this situation, thereby substantially reducing the selectivity of ethylene production when compared with carbon monoxide and carbon dioxide production.

Additionally, while the overall OCM is exothermic, catalysts are used to overcome the endothermic nature of the C—H bond breakage. The endothermic nature of the bond breakage is due to the chemical stability of methane, which is a chemically stable molecule owing to the presence of its four strong tetrahedral C—H bonds (435 kJ/mol). When catalysts are used in the OCM, the exothermic reaction can lead to a large increase in catalyst bed temperature and uncontrolled heat excursions that can lead to catalyst deactivation and a further decrease in ethylene selectivity. Furthermore, the produced ethylene is highly reactive and can form unwanted and thermodynamically favored deep oxidation products.

Generally, in the OCM, $CH_4$ is first oxidatively converted into ethane ($C_2H_6$), and then into $C_2H_4$. $CH_4$ is activated heterogeneously on a catalyst surface, forming methyl free radicals (e.g., $CH_3\cdot$), which then couple in a gas phase to form $C_2H_6$. $C_2H_6$ subsequently undergoes dehydrogenation to form $C_2H_4$. An overall yield of desired $C_2$ hydrocarbons is reduced by non-selective reactions of methyl radicals with oxygen on the catalyst surface and/or in the gas phase, which produce (undesirable) carbon monoxide and carbon dioxide. Some of the best reported OCM outcomes encompass a ~20% conversion of methane and ~80% selectivity to desired $C_2$ hydrocarbons.

Synthesis gas (syngas) is a mixture comprising carbon monoxide, carbon dioxide, and hydrogen, and it is generally used as an intermediate in the production of methanol and ammonia, as well as an intermediate in creating synthetic petroleum to use as a lubricant or fuel. However, the formation of synthesis gas is strongly endothermic and requires high temperatures, which translates in a high energy input. Thus, there is an ongoing need for the development of OCM processes that can increase the production of ethylene, reduce carbon dioxide emissions, as well as produce syngas.

BRIEF SUMMARY

Disclosed herein is a process for producing ethylene and syngas comprising (a) reacting, via an oxidative coupling of methane (OCM) reaction, a first reactant mixture in a first reaction zone to produce a first product mixture, wherein the first reaction zone comprises an OCM catalyst, wherein the first reactant mixture comprises methane and oxygen, and wherein the first product mixture comprises ethylene, ethane, hydrogen, carbon monoxide, carbon dioxide, and unreacted methane, (b) introducing a second reactant mixture comprising at least a portion of the first product mixture to a second reaction zone to produce a second product mixture, wherein the second reaction zone excludes a catalyst, wherein a common reactor comprises both the first reaction zone and the second reaction zone, wherein at least a portion of ethane of the second reactant mixture undergoes a cracking reaction to produce ethylene, wherein at least a portion of the carbon dioxide of the second reactant mixture undergoes a hydrogenation reaction to carbon monoxide, wherein the second product mixture comprises ethylene, ethane, hydrogen, carbon monoxide, carbon dioxide, and unreacted methane, and wherein an amount of ethylene in the second product mixture is greater than an amount of ethylene in the first product mixture, (c) recovering a methane stream, an ethane stream, a carbon dioxide stream, an ethylene stream, and a syngas stream from at least a portion of the second product mixture, wherein the syngas stream comprises carbon monoxide and hydrogen, and (d) recycling at least a portion of the ethane stream and at least a portion of the carbon dioxide stream to the second reaction zone.

Also disclosed herein is a process for producing ethylene and syngas comprising (a) reacting, via an oxidative coupling of methane (OCM) reaction, a first reactant mixture in a first reaction zone to produce a first product mixture, wherein the first reaction zone comprises an OCM catalyst, wherein the first reactant mixture comprises methane and oxygen, and wherein the first product mixture comprises ethylene, ethane, hydrogen, carbon monoxide, carbon dioxide, and unreacted methane, (b) introducing a second reactant mixture comprising at least a portion of the first product mixture and supplemental ethane and supplemental carbon dioxide to a second reaction zone to produce a second product mixture, wherein the second reaction zone excludes a catalyst, wherein a common reactor comprises both the first reaction zone and the second reaction zone, wherein at least a portion of ethane of the second reactant mixture undergoes a cracking reaction to produce ethylene, wherein at least a portion of the carbon dioxide of the second reactant mixture undergoes a hydrogenation reaction to carbon monoxide, wherein the second product mixture comprises ethylene, ethane, hydrogen, carbon monoxide, carbon dioxide, and unreacted methane, and wherein an amount of ethylene in the second product mixture is greater than an amount of ethylene in the first product mixture, (c) recovering methane, ethane, carbon dioxide, ethylene, and syngas from at least a portion of the second product mixture, wherein the syngas comprises carbon monoxide and hydrogen, and wherein the syngas is characterized by a hydrogen to carbon monoxide molar ratio of from about 0.5:1 to about 0.8:1, and (d) recycling at least a portion of the ethane and/or at least a portion of the carbon dioxide recovered from the at least a portion of the second product mixture as supplemental ethane and/or supplemental carbon dioxide, respectively.

BRIEF DESCRIPTION OF THE DRAWINGS

For a detailed description of the preferred aspects of the disclosed methods, reference will now be made to the accompanying drawing in which:

FIGURE displays a schematic of an ethylene and syngas production system.

DETAILED DESCRIPTION

Figure 1:
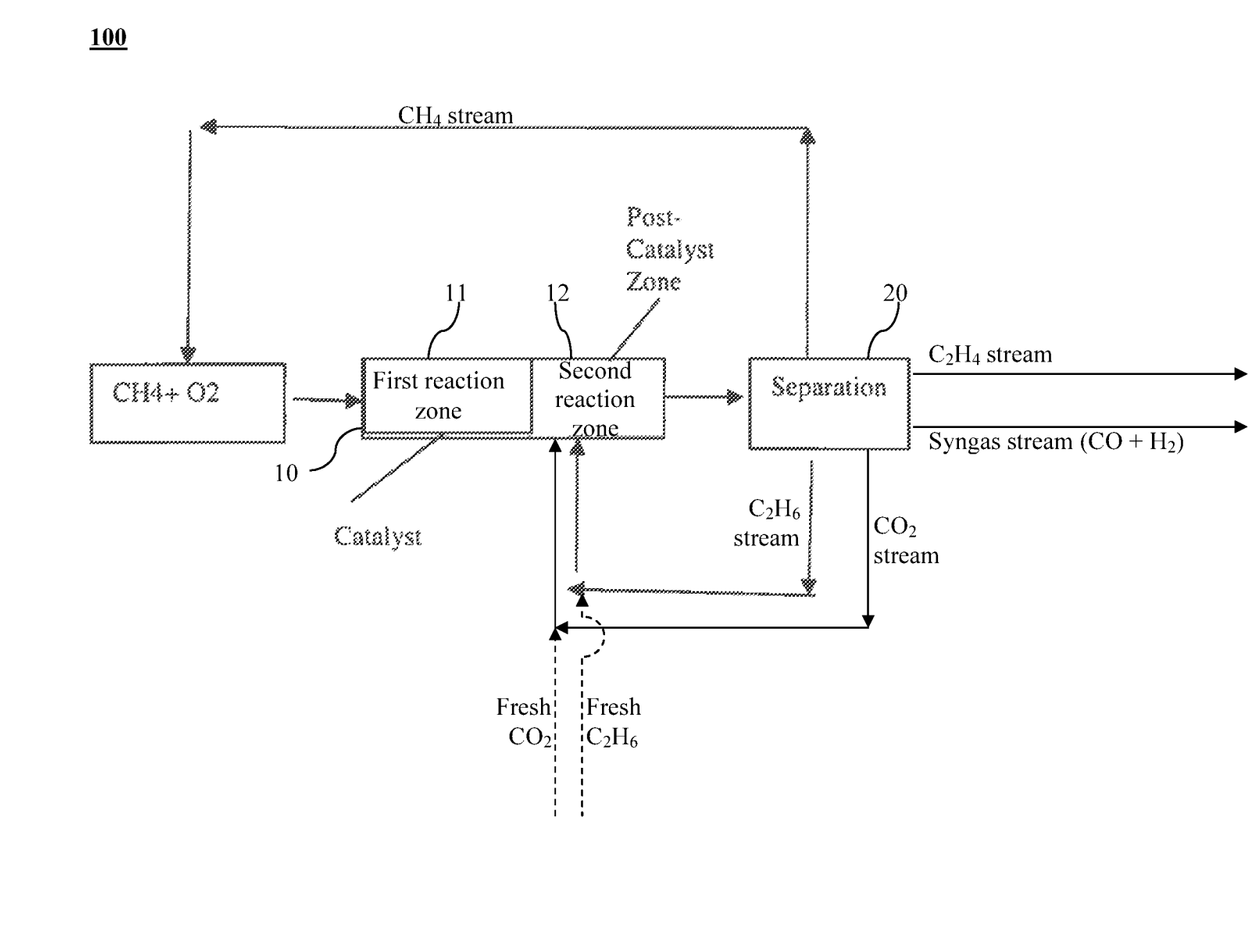

Disclosed herein are processes for producing ethylene and syngas comprising (a) reacting, via an oxidative coupling of methane (OCM) reaction, a first reactant mixture in a first reaction zone to produce a first product mixture, wherein the first reaction zone comprises an OCM catalyst, wherein the first reactant mixture comprises methane and oxygen, and wherein the first product mixture comprises ethylene, ethane, hydrogen, carbon monoxide, carbon dioxide, and unreacted methane; (b) introducing a second reactant mixture comprising at least a portion of the first product mixture to a second reaction zone to produce a second product mixture, wherein the second reaction zone excludes a catalyst, wherein a common reactor comprises both the first reaction zone and the second reaction zone, wherein at least a portion of ethane of the second reactant mixture undergoes a cracking reaction to produce ethylene, wherein at least a portion of the carbon dioxide of the second reactant mixture undergoes a hydrogenation reaction to carbon monoxide, wherein the second product mixture comprises ethylene, ethane, hydrogen, carbon monoxide, carbon dioxide, and unreacted methane, and wherein an amount of ethylene in the second product mixture is greater than an amount of ethylene in the first product mixture; (c) recovering a methane stream, an ethane stream, a carbon dioxide stream, an ethylene stream, and a syngas stream from at least a portion of the second product mixture, wherein the syngas stream comprises carbon monoxide and hydrogen; and (d) recycling at least a portion of the ethane stream and at least a portion of the carbon dioxide stream to the second reaction zone. The recycled ethane stream and/or the recycled carbon dioxide stream can be further contacted with additional ethane and/or additional carbon dioxide during step (d).

Other than in the operating examples or where otherwise indicated, all numbers or expressions referring to quantities of ingredients, reaction conditions, and the like, used in the specification and claims are to be understood as modified in all instances by the term "about." Various numerical ranges are disclosed herein. Because these ranges are continuous, they include every value between the minimum and maximum values. The endpoints of all ranges reciting the same characteristic or component are independently combinable and inclusive of the recited endpoint. Unless expressly indicated otherwise, the various numerical ranges specified in this application are approximations. The endpoints of all ranges directed to the same component or property are inclusive of the endpoint and independently combinable. The term "from more than 0 to an amount" means that the named component is present in some amount more than 0, and up to and including the higher named amount.

The terms "a," "an," and "the" do not denote a limitation of quantity, but rather denote the presence of at least one of the referenced item. As used herein the singular forms "a," "an," and "the" include plural referents.

As used herein, "combinations thereof" is inclusive of one or more of the recited elements, optionally together with a like element not recited, e.g., inclusive of a combination of one or more of the named components, optionally with one or more other components not specifically named that have essentially the same function. As used herein, the term "combination" is inclusive of blends, mixtures, alloys, reaction products, and the like.

Reference throughout the specification to "an aspect," "another aspect," "other aspects," "some aspects," and so forth, means that a particular element (e.g., feature, structure, property, and/or characteristic) described in connection with the aspect is included in at least an aspect described herein, and may or may not be present in other aspects. In addition, it is to be understood that the described element(s) can be combined in any suitable manner in the various aspects.

As used herein, the terms "inhibiting" or "reducing" or "preventing" or "avoiding" or any variation of these terms, include any measurable decrease or complete inhibition to achieve a desired result.

As used herein, the term "effective," means adequate to accomplish a desired, expected, or intended result.

As used herein, the terms "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains") are inclusive or open-ended and do not exclude additional, unrecited elements or method steps.

Unless defined otherwise, technical and scientific terms used herein have the same meaning as is commonly understood by one of skill in the art.

Compounds are described herein using standard nomenclature. For example, any position not substituted by any indicated group is understood to have its valency filled by a bond as indicated, or a hydrogen atom. A dash ("-") that is not between two letters or symbols is used to indicate a point of attachment for a substituent. For example, —CHO is attached through the carbon of the carbonyl group.

Referring to FIGURE, an ethylene and syngas production system 100 is disclosed. The ethylene and syngas production system 100 generally comprises a reactor 10 (e.g., common reactor) comprising a first reaction zone 11 (e.g., catalytic reaction zone) and a second reaction zone 12 (e.g., noncatalytic reaction zone or post-catalytic reaction zone); and a separation unit 20. As will be appreciated by one of skill in the art, and with the help of this disclosure, ethylene and syngas production system components shown in FIGURE can be in fluid communication with each other (as represented by the connecting lines indicating a direction of fluid flow) through any suitable conduits (e.g., pipes, streams, etc.).

In an aspect, a process for producing ethylene and syngas as disclosed herein can comprise reacting, via an oxidative coupling of methane (OCM) reaction, a first reactant mixture in the first reaction zone 11 to produce a first product mixture, wherein the first reaction zone 11 comprises an OCM catalyst, wherein the first reactant mixture comprises methane ($CH_4$) and oxygen ($O_2$), and wherein the first product mixture comprises ethylene ($C_2H_4$), ethane ($C_2H_6$), hydrogen ($H_2$), carbon monoxide (CO), carbon dioxide ($CO_2$), and unreacted methane.

In an aspect, the reactor 10 (e.g., OCM reactor, common reactor) can comprise an adiabatic reactor, an autothermal reactor, a tubular reactor, a continuous flow reactor, and the like, or combinations thereof. The reactor 10 can be characterized by a pressure of from about ambient pressure (e.g., atmospheric pressure) to about 500 psig, alternatively from about ambient pressure to about 200 psig, or alternatively from about ambient pressure to about 100 psig. In an aspect, the method for producing ethylene and syngas as disclosed herein can be carried out at ambient pressure.

In an aspect, the OCM reaction can be conducted in the first reaction zone 11 at a temperature of from about 750° C. to about 900° C., alternatively from about 775° C. to about 875° C., or alternatively from about 800° C. to about 850° C.

The OCM catalyst can comprise one or more oxides, such as basic oxides; mixtures of basic oxides; redox elements; redox elements with basic properties; mixtures of redox elements with basic properties; mixtures of redox elements with basic properties promoted with alkali and/or alkaline earth metals; rare earth metal oxides; mixtures of rare earth metal oxides; mixtures of rare earth metal oxides promoted by alkali and/or alkaline earth metals; manganese; manganese compounds; lanthanum; lanthanum compounds; sodium; sodium compounds; cesium; cesium compounds; calcium; calcium compounds; and the like; or combinations thereof.

In an aspect, the OCM catalysts suitable for use in the present disclosure can be supported catalysts and/or unsupported catalysts. In some aspects, the supported catalysts can comprise a support, wherein the support can be catalytically active (e.g., the support can catalyze an OCM reaction). For example, the catalytically active support can comprise a metal oxide support, such as MgO. In other aspects, the supported catalysts can comprise a support, wherein the support can be catalytically inactive (e.g., the support cannot catalyze an OCM reaction), such as $SiO_2$. In yet other aspects, the supported catalysts can comprise a catalytically active support and a catalytically inactive support.

In some aspects, the support comprises an inorganic oxide, alpha, beta or theta alumina ($Al_2O_3$), activated $Al_2O_3$, silicon dioxide ($SiO_2$), titanium dioxide ($TiO_2$), magnesium oxide (MgO), calcium oxide (CaO), strontium oxide (SrO), zirconium oxide ($ZrO_2$), zinc oxide (ZnO), lithium aluminum oxide ($LiAlO_2$), magnesium aluminum oxide ($MgAlO_4$), manganese oxides (MnO, $MnO_2$, $Mn_3O_4$), lanthanum oxide ($La_2O_3$), activated carbon, silica gel, zeolites, activated clays, silicon carbide (SiC), diatomaceous earth, magnesia, aluminosilicates, calcium aluminate, carbonates, $MgCO_3$, $CaCO_3$, $SrCO_3$, $BaCO_3$, $Y_2(CO_3)_3$, $La_2(CO_3)_3$, and the like, or combinations thereof. In an aspect, the support can comprise MgO, $Al_2O_3$, $SiO_2$, $ZrO_2$, and the like, or combinations thereof.

Nonlimiting examples of OCM catalysts suitable for use in the present disclosure include $CeO_2$, $La_2O_3$—$CeO_2$, $Ca/CeO_2$, $Mn/Na_2WO_4$, $Li_2O$, $Na_2O$, $Cs_2O$, $WO_3$, $Mn_3O_4$, CaO, MgO, SrO, BaO, CaO—MgO, CaO—BaO, Li/MgO, MnO, $W_2O_3$, $SnO_2$, $Yb_2O_3$, $Sm_2O_3$, MnO—$W_2O_3$, MnO—$W_2O_3$—$Na_2O$, MnO—$W_2O_3$—$Li_2O$, $SrO/La_2O_3$, $Ce_2O_3$, La/MgO, $La_2O_3$—$CeO_2$—$Na_2O$, $La_2O_3$—$CeO_2$—CaO, $Na_2O$—MnO—$WO_3$—$La_2O_3$, $La_2O_3$—$CeO_2$—MnO—$WO_3$—SrO, Na—Mn—$La_2O_3/Al_2O_3$, Na—Mn—$O/SiO_2$, $Na_2WO_4$—$Mn/SiO_2$, $Na_2WO_4$—Mn—$O/SiO_2$, Na/Mn/O, $Na_2WO_4$, $Mn_2O_3/Na_2WO_4$, $Mn_3O_4/Na_2WO_4$, $MnWO_4/Na_2WO_4$, $MnWO_4/Na_2WO_4$, $Mn/WO_4$, $Na_2WO_4/Mn$, Sr/Mn—$Na_2WO_4$, and the like, or combinations thereof.

The first reactant mixture can comprise a hydrocarbon or mixtures of hydrocarbons, and oxygen. In some aspects, the hydrocarbon or mixtures of hydrocarbons can comprise natural gas (e.g., $CH_4$), liquefied petroleum gas comprising $C_2$-$C_5$ hydrocarbons, $C_{6+}$ heavy hydrocarbons (e.g., $C_6$ to $C_{24}$ hydrocarbons, such as diesel fuel, jet fuel, gasoline, tars, kerosene, etc.), oxygenated hydrocarbons, biodiesel, alcohols, dimethyl ether, and the like, or combinations thereof. In an aspect, the first reactant mixture can comprise $CH_4$ and $O_2$.

The $O_2$ used in the first reactant mixture can be oxygen gas (which may be obtained via a membrane separation process), technical oxygen (which may contain some air), air, oxygen enriched air, and the like, or combinations thereof.

The first reactant mixture can further comprise a diluent. The diluent is inert with respect to the OCM reaction, e.g., the diluent does not participate in the OCM reaction. In an aspect, the diluent can comprise water, steam, nitrogen, inert gases (e.g., argon), and the like, or combinations thereof. In an aspect, the diluent can be present in the reactant mixture in an amount of from about 0.5% to about 80%, alternatively from about 5% to about 50%, or alternatively from about 10% to about 30%/o, based on the total volume of the first reactant mixture.

In an aspect, the first reactant mixture can be characterized by a $CH_4/O_2$ molar ratio of from about 2:1 to about 10:1, alternatively from about 3:1 to about 9:1, or alternatively from about 4:1 to about 8:1.

In an aspect, the first reaction zone 11 can be characterized by a residence time of from about 10 milliseconds (ms) to about 750 ms, alternatively 10 ms to about 500 ms, alternatively 10 ms to about 100 ms, alternatively 10 ms to about 50 ms, alternatively from about 15 ms to about 45 ms, or alternatively from about 20 ms to about 40 ms. Generally, the residence time of a reaction zone or reactor refers to the average amount of time that a compound (e.g., a molecule of that compound) spends in that particular reaction zone or reactor, e.g., the average amount of time that it takes for a compound (e.g., a molecule of that compound) to travel through the reaction zone or reactor.

In an aspect, the first reaction zone 11 can be characterized by a gas hourly space velocity (GHSV) of from about 3,000 $h^{-1}$ to about 36,000 $h^{-1}$, alternatively from about 5,000 $h^{-1}$ to about 34,000 $h^{-1}$, or alternatively from about 10,000 $h^{-1}$ to about 30,000 $h^{-1}$. Generally, the GHSV relates a reactant (e.g., reactant mixture, first reactant mixture, second reactant mixture, etc.) gas flow rate to a reaction zone (e.g., first reaction zone, second reaction zone, etc.) or reactor volume.

In an aspect, a process for producing ethylene and syngas as disclosed herein can comprise introducing a second reactant mixture comprising at least a portion of the first product mixture to the second reaction zone 12 to produce a second product mixture, wherein the second reaction zone 12 excludes a catalyst, wherein the second product mixture comprises ethylene, ethane, hydrogen, carbon monoxide, carbon dioxide, and unreacted methane, and wherein an amount of ethylene in the second product mixture is greater than an amount of ethylene in the first product mixture.

The second reaction zone 12 excludes a catalyst. As will be appreciated by one of skill in the art, and with the help of this disclosure, while there are catalytic processes for hydrocarbon cracking (e.g., ethane cracking) and $CO_2$ hydrogenation, the current disclosure does not utilize a catalyst for ethane cracking and $CO_2$ hydrogenation in the second reaction zone 12; the ethane cracking and $CO_2$ hydrogenation in the second reaction zone 12 as disclosed herein is thermal in contrast to catalyzed.

In an aspect, at least a portion of ethane of the second reactant mixture can undergo a cracking reaction to produce ethylene in the second reaction zone 12. Generally, a cracking reaction refers to a reaction by which a saturated hydrocarbon or mixture of saturated hydrocarbons is broken down into smaller molecules and/or unsaturated molecules. In the case of ethane cracking, $C_2H_6$ is converted to $C_2H_4$ and $H_2$ according to reaction (1):

$$C_2H_6 = C_2H_4 + H_2 \tag{1}$$

Ethane cracking can provide for an increased amount of $H_2$ in the second reaction zone 12, which in turn can provide for at least a portion of the $H_2$ necessary to hydrogenate $CO_2$ in the second reaction zone 12, which overall can lead to a higher amount of syngas ($H_2$ and CO) in the second product mixture. Cracking can be done in the presence of steam, and in this case it can be referred to as "steam cracking." As will be appreciated by one of skill in the art, and with the help of this disclosure, steam for cracking can be supplied by the second reactant mixture that contains at least a portion of the water from the first product mixture. Further, as will be appreciated by one of skill in the art, and with the help of this disclosure, steam for cracking can be supplied by the $CO_2$ hydrogenation reaction. As will be appreciated by one of skill in the art, and with the help of this disclosure, if water from the first product mixture and/or water produced by the $CO_2$ hydrogenation reaction is not sufficient for the needs of the steam cracking, additional steam can be introduced into the second reaction zone 12 as necessary. In an aspect, steam can be optionally introduced to the second reaction zone 12, for example via a dedicated steam feed line to the second reaction zone and/or via addition to an existing feed stream (e.g., ethane and/or $CO_2$ stream) to the second reaction zone.

In an aspect, at least a portion of the carbon dioxide of the second reactant mixture can undergo a hydrogenation reaction to carbon monoxide in the second reaction zone 12 according to reaction (2):

$$H_2 + CO_2 = CO + H_2O \tag{2}$$

$CO_2$ hydrogenation can provide for an increased amount of CO in the second reaction zone 12, which overall can lead to a higher amount of syngas ($H_2$ and CO) in the second product mixture. The amount of hydrogen present in the second reaction zone 12 will determine the $H_2$/CO molar ratio in the second product mixture, as can be seen from reactions (3) and (4):

$$3H_2 + CO_2 = CO + 2H_2 + H_2O \tag{3}$$

$$4H_2 + CO_2 = CO + 3H_2 + H_2O \tag{4}$$

Reaction (2) is an equilibrium controlled reaction which depends on the $H_2/CO_2$ ratio, as it can be seen from reactions (3) and (4). Reactions (1) and (2) are endothermic, requiring relatively high temperatures, and as such reactions (1) and (2) can utilize the heat produced by the exothermic catalytic OCM reaction.

In an aspect, the second reactant mixture can comprise at least a portion of the first product mixture and supplemental ethane and supplemental $CO_2$.

In some aspects, the supplemental ethane can comprise ethane recovered from the second product mixture, as will be described in more detail later herein. In other aspects, the supplemental ethane can comprise ethane (e.g., fresh ethane) from a source other that the ethane recovered from the second product mixture. In yet other aspects, the supplemental ethane can comprise both (i) ethane recovered from the second product mixture; and (ii) fresh ethane.

In some aspects, the supplemental $CO_2$ can comprise $CO_2$ recovered from the second product mixture, as will be described in more detail later herein. In other aspects, the supplemental $CO_2$ can comprise $CO_2$ (e.g., fresh $CO_2$) from a source other that the $CO_2$ recovered from the second product mixture. In yet other aspects, the supplemental $CO_2$ can comprise both (i) $CO_2$ recovered from the second product mixture; and (ii) fresh $CO_2$.

In some aspects, the supplemental ethane and the supplemental $CO_2$ can be introduced to the second reaction zone 12 via a common stream. In other aspects, the supplemental ethane and the supplemental $CO_2$ can be introduced to the second reaction zone 12 via separate (e.g., distinct, different) streams.

The first product mixture can comprise ethane in an amount of from about 1 mol % to about 20 mol %, alternatively from about 2.5 mol % to about 15 mol %, alternatively from about 5 mol % to about 10 mol %, or alternatively from about 5 mol % to about 7.5 mol %.

The first product mixture can comprise $CO_2$ in an amount of from about 1 mol % to about 20 mol %, alternatively from about 5 mol % to about 15 mol %, alternatively from about 7 mol % to about 13 mol %, or alternatively from about 8 mol % to about 12 mol %.

The first product mixture can be characterized by a $CO_2$/ethane molar ratio of from about 0.8:1 to about 4.0:1, alternatively from about 1.0:1 to about 3.0:1, alternatively from about 1.3:1 to about 2.5:1, alternatively from about 1.5:1 to about 2.0:1, or alternatively from about 1.6:1 to about 1.7:1.

The second reactant mixture can be characterized by a $CO_2$/ethane molar ratio of from about 0.8:1 to about 4.0:1, alternatively from about 1.0:1 to about 3.0:1, alternatively from about 1.3:1 to about 2.5:1, alternatively from about 1.5:1 to about 2.0:1, or alternatively from about 1.6:1 to about 1.7:1. The $CO_2$/ethane molar ratio of the first product mixture and the $CO_2$/ethane molar ratio of the second reactant mixture can be the same or different.

In an aspect, the supplemental ethane and supplemental $CO_2$ can be introduced to the second reaction zone 12 at a $CO_2$/ethane molar ratio of from about 0.8:1 to about 4.0:1, alternatively from about 1.0:1 to about 3.0:1, alternatively from about 1.3:1 to about 2.5:1, alternatively from about 1.5:1 to about 2.0:1, or alternatively from about 1.6:1 to about 1.7:1.

In aspects where the ethane recovered from the second product mixture is not enough for the amount of ethane necessary to be introduced to the second reaction zone 12 and/or the ethane recovered from the second product mixture cannot provide for the desired $CO_2$/ethane molar ratio (e.g., from about 0.8:1 to about 4.0:1) in the second reactant mixture, fresh ethane can be introduced to the second reaction zone 12.

In aspects where the $CO_2$ recovered from the second product mixture is not enough for the amount of $CO_2$ necessary to be introduced to the second reaction zone 12 and/or the $CO_2$ recovered from the second product mixture cannot provide for the desired $CO_2$/ethane molar ratio (e.g., from about 0.8:1 to about 4.0:1) in the second reactant mixture, fresh $CO_2$ can be introduced to the second reaction zone 12.

The second reactant mixture can be characterized by an ethane to methane molar ratio of from about 0.02:1 to about 0.04:1, alternatively from about 0.05:1 to about 0.06:1, alternatively from about 0.02:1 to about 0.07:1, or alternatively from about 0.03:1 to about 0.07:1.

The second reactant mixture can be characterized by a $CO_2$ to methane molar ratio of from about 0.04:1 to about 0.06:1, alternatively from about 0.08:1 to about 0.1:1, alternatively from about 0.04:1 to about 0.2:1, or alternatively from about 0.1:1 to about 0.2:1.

Reactor 10 (e.g., common reactor) comprises both the first reaction zone 11 and the second reaction zone 12. In some aspects, the reactor 10 can comprise the first reaction zone 11 spanning across a first length of the reactor 10, and the second reaction zone 12 spanning across a second length of the reactor 10, wherein the first length plus the second length can sum up to a total length of the reactor 10. As will be appreciated by one of skill in the art, and with the help of this disclosure, the first reaction zone 11 and the second reaction zone 12 in the common reactor 10 can be controlled by controlling the residence time in each of the reaction zones of a mixture traveling through the reactor 10.

In some aspects, a boundary area between the first reaction zone 11 and the second reaction zone 12 can be a variable transitional boundary area (as opposed to a fixed, defined boundary, as it would be in the case when each of the first and the second reaction zones would be contained in different reactors, and not a common reactor). Products from the first reaction zone 11 are communicated to the second reaction zone 12 via the first product mixture. Depending on the type and configuration of the reactor 10 used, the first product mixture may not be isolatable, owing to both the first reaction zone 11 and the second reaction zone 12 being contained in the reactor 10.

The first reaction zone 11 can comprise a catalyst bed comprising the OCM catalyst. As will be appreciated by one of skill in the art, and with the help of this disclosure, the first reaction zone 11 can be considered to end where the catalyst bed ends, and the second reaction zone 12 can be considered to begin where the catalyst bed ends. The second reaction zone 12 is proximate to the end of the catalyst bed contained in the first reaction zone 11. For purposes of the disclosure herein, the beginning and the end of a reaction zone (or catalyst bed contained in a reaction zone) are relative to the direction of flow through the reactor 10.

The first reaction zone 11 can comprise first reaction zone inlet feed streams for the first reactant mixture, wherein the first reaction zone inlet feed streams can be located upstream of the catalyst bed. The methane and oxygen can be introduced to the first reaction zone 11 upstream of the catalyst bed. For purposes of the disclosure herein, the terms "upstream" and "downstream" are relative to the direction of flow through the reactor 10.

The second reaction zone 12 can comprise second reaction zone inlet feed streams for the supplemental ethane and supplemental $CO_2$, wherein the second reaction zone inlet feed streams can be located downstream (e.g., immediately downstream) of the first reaction zone 11, e.g., downstream or immediately downstream of the catalyst bed. The second reaction zone inlet feed streams can be located downstream (e.g., immediately downstream) of the boundary area between the first reaction zone 11 and the second reaction zone 12, e.g., downstream or immediately downstream of the catalyst bed.

The first reaction zone 11 and the second reaction zone 12 can be characterized by the same temperature and pressure.

In some aspects, the pressure in the first reaction zone 11 and the pressure in the second reaction zone 12 can be the same. In other aspects, the pressure in the first reaction zone 11 and the pressure in the second reaction zone 12 can be different.

In some aspects, the temperature in the first reaction zone 11 and the temperature in the second reaction zone 12 can be the same. In other aspects, the temperature in the first reaction zone 11 and the temperature in the second reaction zone 12 can be different. In an aspect, the second reaction zone 12 can be characterized by temperature of from about 750° C. to about 900° C., alternatively from about 775° C. to about 875° C., or alternatively from about 800° C. to about 850° C.

In an aspect, the second reaction zone 12 can be characterized by a residence time of from about 100 ms to about 2.5 seconds (s), alternatively from about 100 ms to about 1 s, alternatively from about 150 ms to about 900 ms, or alternatively from about 250 ms to about 750 ms.

In an aspect, the second reaction zone 12 can be characterized by a GHSV of from about 500 $h^{-1}$ to about 30,000 $h^{-1}$, alternatively from about 750 $h^{-1}$ to about 30,000 $h^{-1}$, alternatively from about 1,000 $h^{-1}$ to about 30,000 $h^{-1}$, alternatively from about 2,500 $h^{-1}$ to about 30,000 $h^{-1}$, alternatively from about 5,000 $h^{-1}$ to about 30,000 $h^{-1}$, alternatively from about 500 $h^{-1}$ to about 5,000 $h^{-1}$, alternatively from about 7,200 $h^{-1}$ to about 30,000 $h^{-1}$, alternatively from about 10,000 $h^{-1}$ to about 27,500 $h^{-1}$, or alternatively from about 12,500 $h^{-1}$ to about 25,000 $h^{-1}$.

In an aspect, a process for producing ethylene and syngas as disclosed herein can comprise introducing at least a portion of the second product mixture to the separation unit 20 for recovering a methane stream, an ethane stream, a $CO_2$ stream, an ethylene stream, and a syngas stream, wherein the syngas stream comprises carbon monoxide and hydrogen. The syngas stream can be characterized by a $H_2$/CO molar ratio of from about 0.5:1 to about 1:1, alternatively from about 0.5:1 to about 0.9:1, or alternatively from about 0.5:1 to about 0.8:1. As will be appreciated by one of skill in the art, and with the help of this disclosure, the recovery of syngas is generally done as a simultaneous recovery of both $H_2$ and CO.

In some aspects, the separation unit 20 can employ distillation and/or cryogenic distillation to produce the methane stream, the ethylene stream, the ethane stream, and the syngas stream; wherein such distillation processes generally occur subsequent to the recovery of the $CO_2$ stream from the second product mixture.

In an aspect, the separation unit 20 can comprise any suitable separators, such as one or more distillation columns (e.g., cryogenic distillation columns); a water removal unit (e.g., a water quench vessel and/or a cooling tower); a $CO_2$ separator; etc.

In some aspects, the second product mixture further comprises water. In such aspects, a process for producing ethylene and syngas as disclosed herein can further comprise separating at least a portion of the water from the second product mixture prior to recovering the methane stream, the ethane stream, the carbon dioxide stream, the ethylene stream, and the syngas stream from the at least a portion of the second product mixture.

In some aspects, the second product mixture can be further compressed (e.g., via a compressor), for example to a pressure in the range of from about 150 psig to about 300 psig, alternatively about 175 psig to about 275 psig, or alternatively about 200 psig to about 250 psig, followed by optionally feeding the compressed second product mixture to a water removal unit. Generally, compressing a gas that contains water to increase its pressure will lead to the water condensing at the increased pressure at an increased temperature as compared to a temperature where water of an otherwise similar gas condenses at pressure lower than the increased pressure. The compressed second product mixture can be further introduced to a water removal unit (e.g., a water quench vessel and/or a cooling tower), where the compressed second product mixture can be further cooled to promote water condensation and removal.

In some aspects, the $CO_2$ stream can be recovered from the second product mixture by using a $CO_2$ separator. The $CO_2$ separator can comprise $CO_2$ removal by amine (e.g., monoethanolamine) absorption (e.g., amine scrubbing), pressure swing adsorption, temperature swing adsorption, gas separation membranes (e.g., porous inorganic membranes, palladium membranes, polymeric membranes, zeolites, etc.), and the like, or combinations thereof. In an aspect, the $CO_2$ separator can comprise $CO_2$ removal by amine absorption.

In an aspect, at least a portion of the methane stream can be recycled to the first reaction zone 11.

In an aspect, a process for producing ethylene and syngas as disclosed herein can comprise recycling at least a portion of the ethane stream and at least a portion of the $CO_2$ stream to the second reaction zone 12. In some aspects, the ethane stream and the $CO_2$ stream can be recycled via a common recycle stream. In other aspects, the ethane stream and the $CO_2$ stream can be recycled via separate (e.g., distinct, different) recycle streams. The ethane stream and the $CO_2$ stream can be recycled to the second reaction zone 12 at a $CO_2$/ethane molar ratio of from about 0.8:1 to about 4.0:1, alternatively from about 1.0:1 to about 3.0:1, alternatively from about 1.3:1 to about 2.5:1, alternatively from about 1.5:1 to about 2.0:1, or alternatively from about 1.6:1 to about 1.7:1. The recycled ethane stream and/or the recycled $CO_2$ stream can be further contacted with additional ethane and/or additional $CO_2$ stream prior to recycling to the second reaction zone 12.

Synthesis gas recovered from the second product mixture can be used for any suitable purpose, such as for producing olefins; for producing methanol; for producing ammonia and fertilizers; in the steel industry; as a fuel source (e.g., for electricity generation); etc.

In some aspects, at least a portion of the syngas stream recovered from the second product mixture can be contacted with a methanol production catalyst in a methanol production unit to produce methanol. A feed stream to the methanol production unit can be characterized by a $H_2/CO$ molar ratio of about 2:1, alternatively about 2.1:1, alternatively from about 1.5:1 to about 2.5:1, alternatively from about 1.8:1 to about 2.3:1, or alternatively from about 2.0:1 to about 2.1:1. The $H_2/CO$ molar ratio of the feed stream to the methanol production unit can be adjusted as necessary to meet the requirements of the methanol production unit, for example by subjecting the syngas stream to a water-gas shift reaction. Generally, the water-gas shift reaction describes the catalytic reaction of carbon monoxide and water vapor to form carbon dioxide and hydrogen according to the reaction $CO + H_2O \rightleftharpoons CO_2 + H_2$. Typically, the water-gas shift reaction is used to increase the $H_2/CO$ molar ratio of gas streams comprising carbon monoxide and hydrogen (e.g., syngas streams). Water-gas shift catalysts can comprise any suitable water-gas shift catalysts, such as commercial water-gas shift catalysts; chromium or copper promoted iron-based catalysts; copper-zinc-aluminum catalyst; and the like; or combinations thereof.

The methanol production unit can comprise any reactor suitable for a methanol synthesis reaction from CO and $H_2$, such as for example an isothermal reactor, an adiabatic reactor, a slurry reactor, a cooled multi tubular reactor, and the like, or combinations thereof.

In an aspect, at least a portion of the CO and at least a portion of the $H_2$ of a feed stream to the methanol production unit (e.g., at least a portion of the syngas stream) can undergo a methanol synthesis reaction. Generally, CO and $H_2$ can be converted into methanol ($CH_3OH$) according to reaction $CO + 2H_2 = CH_3OH$. Methanol synthesis from CO and $H_2$ is a catalytic process, and is most often conducted in the presence of copper based catalysts. The methanol production unit can comprise a methanol production catalyst, such as any suitable commercial catalyst used for methanol synthesis. Nonlimiting examples of methanol production catalysts suitable for use in the methanol production unit in the current disclosure include Cu, Cu/ZnO, $Cu/ThO_2$, $Cu/Zn/Al_2O_3$, $Cu/ZnO/Al_2O_3$, Cu/Zr, and the like, or combinations thereof.

In an aspect, the syngas stream recovered from the second product mixture can be characterized by a $H_2/CO$ molar ratio of about 1:1, wherein at least a portion of the syngas can be used for dimethyl ether production.

In an aspect, the syngas stream recovered from the second product mixture can be characterized by a $H_2/CO$ molar ratio of about 1:1, wherein at least a portion of the syngas stream can be used for oxo-synthesis of aliphatic aldehydes and/or alcohols. In such aspect, the alcohol can comprise 2-ethyl hexanol.

In an aspect, the syngas stream recovered from the second product mixture can be further converted to olefins. For example, the syngas stream can be converted to alkanes by using a Fisher-Tropsch process, and the alkanes can be further converted by dehydrogenation into olefins.

In an aspect, the syngas stream recovered from the second product mixture can be further converted to liquid hydrocarbons (e.g., alkanes) by a Fisher-Tropsch process. In such aspect, the liquid hydrocarbons can be further converted by dehydrogenation into olefins.

In an aspect, the syngas stream recovered from the second product mixture can be further used as fuel to generate power.

In an aspect, the syngas stream recovered from the second product mixture can be further converted to methane via a methanation process.

In some aspects, the ethylene stream recovered from the second product mixture can comprise ethylene and acetylene. At least a portion of the ethylene stream, a polar aprotic solvent, and hydrogen can be introduced to a liquid phase hydrogenation unit, wherein the liquid phase hydrogenation unit comprises an acetylene hydrogenation catalyst, and wherein at least a portion of the acetylene of the ethylene stream can be selectively hydrogenated to produce ethylene.

Nonlimiting examples of polar aprotic solvents suitable for use in the present disclosure include N-methyl-2-pyrrolidone (NMP), N,N-dimethylformamide (DMF), acetone, tetrahydrofuran (THF), dimethylsulfoxide (DMSO), and the like, or combinations thereof.

The liquid phase hydrogenation unit can be any suitable liquid phase hydrogenation reactor, such as a fixed bed catalytic reactor (typically operated adiabatically); and/or a tubular reactor (typically operated isothermally). Generally, the liquid phase hydrogenation unit comprises an acetylene hydrogenation catalyst, such as a palladium (Pd) based catalyst, which can be supported on alumina, zeolites, etc. The hydrogenation catalyst can further comprise other metals, such as platinum, silver, nickel, etc. In an aspect, the acetylene hydrogenation catalyst can comprise $Pd/Al_2O_3$. Liquid phase hydrogenation of acetylene processes are described in more detail in U.S. Pat. No. 4,128,595, which is incorporated by reference herein in its entirety.

In an aspect, a process for producing ethylene and syngas can comprise (a) reacting, via an OCM reaction, a first reactant mixture in a first reaction zone to produce a first product mixture, wherein the first reaction zone comprises an OCM catalyst, wherein the first reactant mixture comprises methane and oxygen, and wherein the first product mixture comprises ethylene, ethane, hydrogen, carbon monoxide, carbon dioxide, and unreacted methane; (b) introducing a second reactant mixture comprising at least a portion of the first product mixture and supplemental ethane and supplemental carbon dioxide to a second reaction zone to produce a second product mixture, wherein the second reaction zone excludes a catalyst, wherein a common reactor comprises both the first reaction zone and the second reaction zone, wherein the common reactor is characterized by a temperature of from about 750° C. to about 900° C., wherein at least a portion of ethane of the second reactant mixture undergoes a cracking reaction to produce ethylene and hydrogen, wherein at least a portion of the carbon dioxide of the second reactant mixture undergoes a hydrogenation reaction to carbon monoxide with the hydrogen from the first product mixture and/or the hydrogen from the cracking reaction, wherein the second product mixture comprises ethylene, ethane, hydrogen, carbon monoxide, carbon dioxide, and unreacted methane, and wherein an amount of ethylene in the second product mixture is greater than an amount of ethylene in the first product mixture; (c) recovering methane, ethane, carbon dioxide, ethylene, and syngas from at least a portion of the second product mixture, wherein the syngas comprises carbon monoxide and hydrogen, and wherein the syngas is characterized by a hydrogen to carbon monoxide molar ratio of from about 0.5:1 to about 0.8:1; and (d) recycling at least a portion of the ethane and/or at least a portion of the carbon dioxide recovered from the at least a portion of the second product mixture as supplemental ethane and/or supplemental carbon dioxide, respectively.

In an aspect, a process for producing ethylene and syngas as disclosed herein can advantageously display improvements in one or more process characteristics when compared to an otherwise similar process that does not integrate OCM with other processes for producing desired products. Ethane cracking and $CO_2$ hydrogenation as disclosed herein can advantageously increase ethylene and syngas production, wherein syngas can be further converted to useful products, such as methanol, thereby further increasing the overall efficiency of the process.

In an aspect, a process for producing ethylene and syngas as disclosed herein can advantageously utilize the reaction heat of the OCM reaction for ethane cracking and $CO_2$ hydrogenation. Further, by recycling $CO_2$ to the hydrogenation zone, $CO_2$ emissions can be reduced. Additional advantages of the processes for the production of ethylene and syngas as disclosed herein can be apparent to one of skill in the art viewing this disclosure.

EXAMPLES

The subject matter having been generally described, the following examples are given as particular embodiments of the disclosure and to demonstrate the practice and advantages thereof. It is understood that the examples are given by way of illustration and are not intended to limit the specification of the claims to follow in any manner.

Example 1

Oxidative coupling of methane (OCM) reactions were conducted in the presence of a catalyst as follows. The used catalyst was 12% Na-15% $Mn/SiO_2$, and the reaction temperature was 850° C. The reactor was a quartz fixed bed reactor with a diameter of 7 mm and a length of 12 cm heated by electrical heating, with a catalyst loading of 3 ml in the catalytic zone of the reactor (e.g., first reaction zone), wherein this particular catalyst loading was intended to exhibit less of an adiabatic temperature increase through the fixed bed. The OCM reaction was conducted at a $CH_4/O_2=4$, and at a gas hourly space velocity (GHSV) of 7,200 $h^{-1}$ in the catalytic zone.

The composition of the dry effluent gas recovered from the reactor (after water removal) was: $CH_4$=79.58 mol %; $CO_2$=10.96 mol %; $C_2H_4$=5.33 mol %; $C_2H_6$=6.28 mol %; and CO=0.68 mol %. As it can be seen from the composition of the dry effluent gas recovered from the reactor, the main deep oxidation product was $CO_2$.

The effluent gas recovered from the reactor was further used for the recovery of ethane and $CO_2$. The recovered ethane and the recovered $CO_2$ were recycled to a post-catalytic zone of the reactor at a $CO_2$ to ethane molar ratio of 1.6. The post-catalytic zone of the reactor was also characterized by a temperature of 850° C. (which was the reactor temperature). The post-catalytic zone of the reactor (e.g., second reaction zone) was characterized by a GHSV within 900-3,600 $h^{-1}$, depending on the volume of the post-catalytic zone and/or the flow rate of gases entering the post-catalytic zone. The volume of the post-catalytic zone was 2-4 ml. The contact time (e.g., residence time) within the catalytic zone (e.g., first reaction zone) and the post-catalytic zone (e.g., second reaction zone) was within 0.5-2.5 seconds. The contact time in most cases in the catalytic zone was about 0.5 seconds, and in the post-catalytic zone was about 2 seconds. Separation of ethane and $CO_2$ from effluent gases would be achieved through methods known to one of skill in the art, such as pressure swing adsorption (PSA) for $C_2H_6$, and amine adsorption for $CO_2$.

The $C_2H_6$ conversion was 55.5%, and the $CO_2$ conversion was 40.0%, in the post-catalytic zone. For purposes of the disclosure herein, the conversion of a reagent is a % conversion based on moles converted. For example, the ethane conversion can be calculated by using the following equation:

$$C_2H_6 \text{ conversion} = \frac{C_{C_2H_6}^{in} - C_{C_2H_6}^{out}}{C_{C_2H_6}^{in}} \times 100\%$$

wherein $C_{C_2H_6}^{in}$=number of moles of C from $C_2H_6$ that entered the post-catalytic zone, both from the catalytic zone effluent, and from the recycled ethane; and wherein $C_{C_2H_6}^{out}$=number of moles of C from $C_2H_6$ that was recovered from the reactor from the post-catalytic zone. As another example, the $CO_2$ conversion can be calculated by using the following equation:

$$CO_2 \text{ conversion} = \frac{C_{CO_2}^{in} - C_{CO_2}^{out}}{C_{CO_2}^{in}} \times 100\%$$

wherein $C_{CO_2}^{in}$=number of moles of C from $CO_2$ that entered the post-catalytic zone, both from the catalytic zone effluent, and from the recycled $CO_2$; and wherein $C_{CO_2}^{out}$=number of moles of C from $CO_2$ that was recovered from the reactor from the post-catalytic zone.

For the purpose of any U.S. national stage filing from this application, all publications and patents mentioned in this disclosure are incorporated herein by reference in their entireties, for the purpose of describing and disclosing the constructs and methodologies described in those publications, which might be used in connection with the methods of this disclosure. Any publications and patents discussed herein are provided solely for their disclosure prior to the filing date of the present application. Nothing herein is to be construed as an admission that the inventors are not entitled to antedate such disclosure by virtue of prior invention.

In any application before the United States Patent and Trademark Office, the Abstract of this application is provided for the purpose of satisfying the requirements of 37 C.F.R. § 1.72 and the purpose stated in 37 C.F.R. § 1.72(b) "to enable the United States Patent and Trademark Office and the public generally to determine quickly from a cursory inspection the nature and gist of the technical disclosure." Therefore, the Abstract of this application is not intended to be used to construe the scope of the claims or to limit the scope of the subject matter that is disclosed herein. Moreover, any headings that can be employed herein are also not intended to be used to construe the scope of the claims or to limit the scope of the subject matter that is disclosed herein. Any use of the past tense to describe an example otherwise indicated as constructive or prophetic is not intended to reflect that the constructive or prophetic example has actually been carried out.

The present disclosure is further illustrated by the following examples, which are not to be construed in any way as imposing limitations upon the scope thereof. On the contrary, it is to be clearly understood that resort can be had to various other aspects, embodiments, modifications, and equivalents thereof which, after reading the description herein, can be suggest to one of ordinary skill in the art without departing from the spirit of the present invention or the scope of the appended claims.

ADDITIONAL DISCLOSURE

A first aspect, which is a process for producing ethylene and syngas comprising (a) reacting, via an oxidative coupling of methane (OCM) reaction, a first reactant mixture in a first reaction zone to produce a first product mixture, wherein the first reaction zone comprises an OCM catalyst, wherein the first reactant mixture comprises methane and oxygen, and wherein the first product mixture comprises ethylene, ethane, hydrogen, carbon monoxide, carbon dioxide, and unreacted methane; (b) introducing a second reactant mixture comprising at least a portion of the first product mixture to a second reaction zone to produce a second product mixture, wherein the second reaction zone excludes a catalyst, wherein a common reactor comprises both the first reaction zone and the second reaction zone, wherein at least a portion of ethane of the second reactant mixture undergoes a cracking reaction to produce ethylene, wherein at least a portion of the carbon dioxide of the second reactant mixture undergoes a hydrogenation reaction to carbon monoxide, wherein the second product mixture comprises ethylene, ethane, hydrogen, carbon monoxide, carbon dioxide, and unreacted methane, and wherein an amount of ethylene in the second product mixture is greater than an amount of ethylene in the first product mixture; (c) recovering a methane stream, an ethane stream, a carbon dioxide stream, an ethylene stream, and a syngas stream from at least a portion of the second product mixture, wherein the syngas stream comprises carbon monoxide and hydrogen; and (d) recycling at least a portion of the ethane stream and at least a portion of the carbon dioxide stream to the second reaction zone.

A second aspect, which is the process of the first aspect, wherein the at least a portion of the ethane stream and at least a portion of the carbon dioxide stream are recycled via a common recycle stream.

A third aspect, which is the process of any one of the first and the second aspects, wherein the at least a portion of the ethane stream and at least a portion of the carbon dioxide stream are recycled to the second reaction zone at a carbon dioxide to ethane molar ratio of from about 0.8:1 to about 4.0:1.

A fourth aspect, which is the process of any one of the first through the third aspects, wherein the common reactor comprises an adiabatic reactor, an autothermal reactor, a tubular reactor, a continuous flow reactor, or combinations thereof.

A fifth aspect, which is the process of any one of the first through the fourth aspects, wherein the carbon dioxide stream is separated from the second product mixture by amine absorption.

A sixth aspect, which is the process of any one of the first through the fifth aspects, wherein the second product mixture further comprises water, and wherein step (c) further comprises separating at least a portion of the water from the second product mixture prior to recovering the methane stream, the ethane stream, the carbon dioxide stream, the ethylene stream, and the syngas stream from the at least a portion of the second product mixture.

A seventh aspect, which is the process of any one of the first through the sixth aspects, wherein step (c) further comprises cryogenic distillation to recover the methane stream, the ethane stream, the ethylene stream, and the syngas stream.

An eighth aspect, which is the process of any one of the first through the seventh aspects, wherein at least a portion of the methane stream is recycled to the first reaction zone.

A ninth aspect, which is the process of any one of the first through the eighth aspects, wherein the syngas stream is characterized by a hydrogen to carbon monoxide molar ratio of from about 0.5:1 to about 1:1.

A tenth aspect, which is the process of any one of the first through the ninth aspects, wherein at least a portion of the syngas stream is contacted with a methanol production catalyst to produce methanol.

An eleventh aspect, which is the process of the tenth aspect, wherein the methanol production catalyst comprises Cu, Cu/ZnO, Cu/ThO$_2$, Cu/Zn/Al$_2$O$_3$, Cu/ZnO/Al$_2$O$_3$, Cu/Zr, or combinations thereof.

A twelfth aspect, which is the process of any one of the first through the eleventh aspects, wherein the ethylene stream comprises ethylene and acetylene, wherein at least a portion of the ethylene stream is contacted with an acetylene hydrogenation catalyst, and wherein at least a portion of the acetylene of the ethylene stream is selectively hydrogenated to produce ethylene.

A thirteenth aspect, which is the process of the twelfth aspect, wherein the acetylene hydrogenation catalyst comprises palladium (Pd).

A fourteenth aspect, which is the process of any one of the first through the thirteenth aspects, wherein the OCM catalyst comprises one or more oxides.

A fifteenth aspect, which is the process of the fourteenth aspect, wherein the OCM catalyst comprises $CeO_2$, $La_2O_3$—$CeO_2$, $Ca/CeO_2$, $Mn/Na_2WO_4$, $Li_2O$, $Na_2O$, $Cs_2O$, $WO_3$, $Mn_3O_4$, CaO, MgO, SrO, BaO, CaO—MgO, CaO—BaO, Li/MgO, MnO, $W_2O_3$, $SnO_2$, $Yb_2O_3$, $Sm_2O_3$, MnO—$W_2O_3$, MnO—$W_2O_3$—$Na_2O$, MnO—$W_2O_3$—$Li_2O$, $SrO/La_2O_3$, $La_2O_3$, $Ce_2O_3$, La/MgO, $La_2O_3$—$CeO_2$—$Na_2O$, $La_2O_3$—$CeO_2$—CaO, $Na_2O$—MnO—$WO_3$—$La_2O_3$, $La_2O_3$—$CeO_2$—MnO—$WO_3$—SrO, Na—Mn—$La_2O_3/Al_2O_3$, Na—Mn—$O/SiO_2$, $Na_2WO_4$—$Mn/SiO_2$, $Na_2WO_4$—Mn—$O/SiO_2$, Na/Mn/O, $Na_2WO_4$, $Mn_2O_3/Na_2WO_4$, $Mn_3O_4/Na_2WO_4$, $MnWO_4/Na_2WO_4$, $MnWO_4/Na_2WO_4$, $Mn/WO_4$, $Na_2WO_4/Mn$, $Sr/Mn$—$Na_2WO_4$, or combinations thereof.

A sixteenth aspect, which is the process of any one of the first through the fifteenth aspects, wherein the first reaction zone is characterized by a temperature of from about 750° C. to about 900° C.

A seventeenth aspect, which is the process of any one of the first through the sixteenth aspects, wherein the second reaction zone is characterized by a temperature of from about 750° C. to about 900° C.

An eighteenth aspect, which is the process of any one of the first through the seventeenth aspects, wherein the first reaction zone is characterized by a residence time of from about 10 milliseconds to about 750 milliseconds.

A nineteenth aspect, which is the process of any one of the first through the eighteenth aspects, wherein the second reaction zone is characterized by a residence time of from about 100 milliseconds to about 2.5 seconds.

A twentieth aspect, which is the process of any one of the first through the nineteenth aspects, wherein the first reaction zone is characterized by a gas hourly space velocity of from about 3,000 $h^{-1}$ to about 36,000 $h^{-1}$.

A twenty-first aspect, which is the process of any one of the first through the twentieth aspects, wherein the second reaction zone is characterized by a gas hourly space velocity of from about 500 $h^{-1}$ to about 30,000 $h^{-1}$.

A twenty-second aspect, which is the process of any one of the first through the twenty-first aspects, wherein the common reactor is characterized by a pressure of from about ambient pressure to about 500 psig.

A twenty-third aspect, which is the process of any one of the first through the twenty-second aspects, wherein the first reactant mixture is characterized by a methane to oxygen molar ratio of from about 2:1 to about 10:1.

A twenty-fourth aspect, which is the process of any one of the first through the twenty-third aspects, wherein the recycled ethane stream and/or the recycled carbon dioxide stream are further contacted with additional ethane and/or additional carbon dioxide during step (d).

A twenty-fifth aspect, which is a process for producing ethylene and syngas comprising (a) reacting, via an oxidative coupling of methane (OCM) reaction, a first reactant mixture in a first reaction zone to produce a first product mixture, wherein the first reaction zone comprises an OCM catalyst, wherein the first reactant mixture comprises methane and oxygen, and wherein the first product mixture comprises ethylene, ethane, hydrogen, carbon monoxide, carbon dioxide, and unreacted methane; (b) introducing a second reactant mixture comprising at least a portion of the first product mixture and supplemental ethane and supplemental carbon dioxide to a second reaction zone to produce a second product mixture, wherein the second reaction zone excludes a catalyst, wherein a common reactor comprises both the first reaction zone and the second reaction zone, wherein at least a portion of ethane of the second reactant mixture undergoes a cracking reaction to produce ethylene, wherein at least a portion of the carbon dioxide of the second reactant mixture undergoes a hydrogenation reaction to carbon monoxide, wherein the second product mixture comprises ethylene, ethane, hydrogen, carbon monoxide, carbon dioxide, and unreacted methane, and wherein an amount of ethylene in the second product mixture is greater than an amount of ethylene in the first product mixture; (c) recovering methane, ethane, carbon dioxide, ethylene, and syngas from at least a portion of the second product mixture, wherein the syngas comprises carbon monoxide and hydrogen, and wherein the syngas is characterized by a hydrogen to carbon monoxide molar ratio of from about 0.5:1 to about 0.8:1; and (d) recycling at least a portion of the ethane and/or at least a portion of the carbon dioxide recovered from the at least a portion of the second product mixture as supplemental ethane and/or supplemental carbon dioxide, respectively.

A twenty-sixth aspect, which is the process of the twenty-fifth aspect, wherein the supplemental ethane and/or the supplemental carbon dioxide introduced to the second reaction zone further comprises ethylene and/or carbon dioxide, respectively from a source other than the recovering from step (c).

A twenty-seventh aspect, which is the process of any one of the twenty-fifth and the twenty-sixth aspects, wherein the supplemental ethane and supplemental carbon dioxide are introduced to the second reaction zone at a carbon dioxide to ethane molar ratio of from about 0.8:1 to about 4.0:1.

A twenty-eighth aspect, which is the process of any one of the twenty-fifth through the twenty-seventh aspects, wherein the second reactant mixture is characterized by an ethane to methane molar ratio of from about 0.03:1 to about 0.07:1.

A twenty-ninth aspect, which is the process of any one of the twenty-fifth through the twenty-eighth aspects, wherein the second reactant mixture is characterized by a carbon dioxide to methane molar ratio of from about 0.1:1 to about 0.2:1.

While embodiments of the disclosure have been shown and described, modifications thereof can be made without departing from the spirit and teachings of the invention. The embodiments and examples described herein are exemplary only, and are not intended to be limiting. Many variations and modifications of the invention disclosed herein are possible and are within the scope of the invention.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the detailed description of the present invention. The disclosures of all patents, patent applications, and publications cited herein are hereby incorporated by reference.

What is claimed is:

1. A process for producing ethylene and syngas comprising:
   (a) reacting, via an oxidative coupling of methane (OCM) reaction, a first reactant mixture in a first reaction zone to produce a first product mixture, wherein the first reaction zone comprises an OCM catalyst, wherein the first reactant mixture comprises methane and oxygen, and wherein the first product mixture comprises ethylene, ethane, hydrogen, carbon monoxide, carbon dioxide, and unreacted methane;
   (b) introducing a second reactant mixture comprising at least a portion of the first product mixture to a second reaction zone to produce a second product mixture, wherein the second reactant mixture is characterized by an ethane to methane molar ratio of from about 0.02:1 to about 0.07:1, wherein the second reactant mixture is characterized by a carbon dioxide to methane molar ratio of from about 0.04:1 to about 0.2:1, wherein the second reaction zone excludes a catalyst, wherein a common reactor comprises both the first reaction zone and the second reaction zone, wherein at least a portion of ethane of the second reactant mixture undergoes a cracking reaction to produce ethylene, wherein at least a portion of the carbon dioxide of the second reactant mixture undergoes a hydrogenation reaction to carbon monoxide, wherein the second product mixture comprises ethylene, ethane, hydrogen, carbon monoxide, carbon dioxide, and unreacted methane, and wherein an amount of ethylene in the second product mixture is greater than an amount of ethylene in the first product mixture;
   (c) recovering a methane stream, an ethane stream, a carbon dioxide stream, an ethylene stream, and a syngas stream from at least a portion of the second product mixture, wherein the syngas stream comprises carbon monoxide and hydrogen, and wherein the syngas stream is characterized by a hydrogen to carbon monoxide molar ratio of from about 0.5:1 to about 1:1; and
   (d) recycling at least a portion of the ethane stream and at least a portion of the carbon dioxide stream to the second reaction zone.

2. The process of claim 1, wherein the at least a portion of the ethane stream and at least a portion of the carbon dioxide stream are recycled via a common recycle stream.

3. The process of claim 1, wherein the at least a portion of the ethane stream and at least a portion of the carbon dioxide stream are recycled to the second reaction zone at a carbon dioxide to ethane molar ratio of from about 0.8:1 to about 4.0:1.

4. The process of claim 1, wherein the common reactor comprises an adiabatic reactor, an autothermal reactor, a tubular reactor, a continuous flow reactor, or combinations thereof.

5. The process of claim 1, wherein the carbon dioxide stream is separated from the second product mixture by amine absorption.

6. The process of claim 1, wherein the second product mixture further comprises water, and wherein step (c) further comprises separating at least a portion of the water from the second product mixture prior to recovering the methane stream, the ethane stream, the carbon dioxide stream, the ethylene stream, and the syngas stream from the at least a portion of the second product mixture.

7. The process of claim 1, wherein step (c) further comprises cryogenic distillation to recover the methane stream, the ethane stream, the ethylene stream, and the syngas stream.

8. The process of claim 1, wherein at least a portion of the methane stream is recycled to the first reaction zone.

9. The process of claim 1, wherein the syngas stream is characterized by a hydrogen to carbon monoxide molar ratio of from about 0.5:1 to about 0.8:1.

10. The process of claim 1, wherein at least a portion of the syngas stream is contacted with a methanol production catalyst to produce methanol.

11. The process of claim 1, wherein the ethylene stream comprises ethylene and acetylene, wherein at least a portion of the ethylene stream is contacted with an acetylene hydrogenation catalyst, wherein at least a portion of the acetylene of the ethylene stream is selectively hydrogenated to produce ethylene.

12. The process of claim 1, wherein the first reaction zone is characterized by a temperature of from about 750° C. to about 900° C., and wherein the second reaction zone is characterized by a temperature of from about 750° C. to about 900° C.

13. The process of claim 1, wherein the first reaction zone is characterized by a residence time of from about 10 milliseconds to about 750 milliseconds.

14. The process of claim 1, wherein the second reaction zone is characterized by a residence time of from about 100 milliseconds to about 2.5 seconds.

15. The process of claim 1, wherein the first reaction zone is characterized by a gas hourly space velocity of from about 3,000 $h^{-1}$ to about 36,000 $h^{-1}$, and wherein the second reaction zone is characterized by a gas hourly space velocity of from about 500 $h^{-1}$ to about 30,000 $h^{-1}$.

16. The process of claim 1, wherein the recycled ethane stream and/or the recycled carbon dioxide stream are further contacted with additional ethane and/or additional carbon dioxide during step (d).

17. A process for producing ethylene and syngas comprising:
   (a) reacting, via an oxidative coupling of methane (OCM) reaction, a first reactant mixture in a first reaction zone to produce a first product mixture, wherein the first reaction zone comprises an OCM catalyst, wherein the first reactant mixture comprises methane and oxygen, and wherein the first product mixture comprises ethylene, ethane, hydrogen, carbon monoxide, carbon dioxide, and unreacted methane;
   (b) introducing a second reactant mixture comprising at least a portion of the first product mixture and supplemental ethane and supplemental carbon dioxide to a second reaction zone to produce a second product mixture, wherein the second reactant mixture is characterized by a carbon dioxide to ethane molar ratio of from about 1.5:1 to about 2.0:1, wherein the second reaction zone excludes a catalyst, wherein a common reactor comprises both the first reaction zone and the second reaction zone, wherein at least a portion of ethane of the second reactant mixture undergoes a cracking reaction to produce ethylene, wherein at least a portion of the carbon dioxide of the second reactant mixture undergoes a hydrogenation reaction to carbon monoxide, wherein the second product mixture comprises ethylene, ethane, hydrogen, carbon monoxide, carbon dioxide, and unreacted methane, and wherein an amount of ethylene in the second product mixture is greater than an amount of ethylene in the first product mixture;

(c) recovering methane, ethane, carbon dioxide, ethylene, and syngas from at least a portion of the second product mixture, wherein the syngas comprises carbon monoxide and hydrogen, and wherein the syngas is characterized by a hydrogen to carbon monoxide molar ratio of from about 0.5:1 to about 0.8:1; and (d) recycling at least a portion of the ethane and/or at least a portion of the carbon dioxide recovered from the at least a portion of the second product mixture as supplemental ethane and/or supplemental carbon dioxide, respectively.

18. The process of claim 17, wherein the supplemental ethane and/or the supplemental carbon dioxide introduced to the second reaction zone further comprises ethylene and/or carbon dioxide, respectively from a source other than the recovering from step (c).

19. The process of claim 17, wherein the supplemental ethane and supplemental carbon dioxide are introduced to the second reaction zone at a carbon dioxide to ethane molar ratio of from about 0.8:1 to about 4.0:1.

20. The process of claim 17, wherein the second reactant mixture is characterized by an ethane to methane molar ratio of from about 0.03:1 to about 0.07:1, and wherein the second reactant mixture is characterized by a carbon dioxide to methane molar ratio of from about 0.1:1 to about 0.2:1.

* * * * *